United States Patent [19]

Farina et al.

[11] Patent Number: 4,908,456

[45] Date of Patent: Mar. 13, 1990

[54] PROCESS FOR PREPARING METHYLOLATED HYDANTOINS

[75] Inventors: Thomas E. Farina, Montoursville; Lloyd C. Franklin, Montgomery, both of Pa.

[73] Assignees: Takatori Corporation; Takatori Hitech Co., Ltd., both of Nara, Japan

[21] Appl. No.: 333,588

[22] Filed: Apr. 5, 1989

[51] Int. Cl.$^4$ .................. C07D 233/72; C07D 233/78
[52] U.S. Cl. ..................................... 548/312; 548/313
[58] Field of Search ............................... 548/312, 313

[56] References Cited

U.S. PATENT DOCUMENTS 3,987,184  10/1976  Foelsch ........................... 548/312 X

FOREIGN PATENT DOCUMENTS 63-275568  11/1988  Japan .

Primary Examiner—Richard A. Schwartz
Attorney, Agent, or Firm—Wenderoth, Lind & Ponack

[57] ABSTRACT

A method for making methylolated hydantoins by reacting a hydantoin, a formaldehyde such as paraformaldehyde and an alkaline catalyst at conditions of temperature and pressure sufficient to induce reaction to obtain a product in essentially 100% active form. Dry methylolated hydantoin product made by this process may be stored or shipped more economically than an aqueous solution containing a methylolated hydantoin.

20 Claims, No Drawings

PROCESS FOR PREPARING METHYLOLATED HYDANTOINS

BACKGROUND OF THE INVENTION

This invention relates to the production of a methylolated hydantoin from a hydantoin and a non-aqueous formaldehyde, e.g., paraformaldehyde. More particularly, this invention relates to the production of a crystallized methylolated hydantoin from hydantoin derivatives and paraformaldehyde under certain conditions in which the reaction diluent used, if any, is the product itself. Using this method, a dry, relatively pure product is obtained without the need for a separation process to remove a reaction medium.

Methylolated hydantoins are colorless, odorless, water-soluble compounds used as formaldehyde donors or cross-linking agents in various industrial systems and commercial products. For example, the textile industry uses 5,5-dimethylhydantoin-formaldehyde adducts to make crease-resistant cotton. In the cosmetic industry, 1,3-dimethylol-5,5-dimethylhydantoin (DMDMH) is used as a preservative. DMDMH has been proven an effective antimicrobial agent that is safe for handlers, users and the environment when used under proper conditions.

Several methods for the production of the condensate product of 5,5-dimethylhydantoin and formaldehyde have been suggested in the past. Japanese Patent No. 4709 (1966) discloses preparing DMDMH in an aqueous solution by mixing one mole of dimethylhydantoin and three to five aqueous moles of formaldehyde (37% by weight), heating the mixture at 80° C. for 25 to 30 minutes, and stirring. No catalyst is needed for the reaction. U.S. Pat. No. 3,987,184 describes a process for the production of an aqueous solution of DMDMH by reacting a ratio of 1.85 to 4.2 moles of formaldehyde per mole of dimethylhydantoin in water. The pH of the solution is adjusted to be within the range of 7 to 9, and the reaction takes place at 22° to 65° C.

As shown by the above-mentioned patents, the methods of producing methylolated hydantoins, particularly DMDMH, have generally involved reactions in an aqueous solution. The resulting product is usually transported as a liquid and used as an aqueous solution. Thus, costs include solvent and the expense of transporting volumes that include not only the DMDMH itself, but also the aqueous solution. If a dry product is desired, a tedious, time-consuming, separation process would be required as an additional production step.

Another disadvantage of the prior methods involving reactions in aqueous medium is that the hydantoin must have sufficient water solubility to effect reaction between the hydantoin and aqueous formaldehyde. Thus, reactions of hydantoins which are substituted with alkyl groups >$C_2$ at the 5-position cannot readily be carried out.

Accordingly, it is the primary object of the present invention to produce economically a methylolated hydantoin product in essentially 100% active form which can be transported as a solid.

Another object of this invention is to produce a methylolated hydantoin in relatively pure form without the resulting formation of by-products.

A further object of this invention is to produce an effectively dry methylolated hydantoin product without using a separation or drying technique to isolate the final product.

It is yet another object of this invention to produce methylolated hydantoins in relatively pure form that are not readily prepared by prior art techniques.

These and other objects of our invention will be apparent from the discussion which follows.

SUMMARY OF THE INVENTION

We have discovered a method of making a dry, crystallized methylolated hydantoin product in essentially 100% active form, e.g., a non-solvated form. A hydantoin, a source of formaldehyde, such as paraformaldehyde, and an alkaline catalyst are mixed and reacted at elevated temperatures. This reaction is conducted in the effective absence of water other than that associated, as a hydrate, with the source of formaldehyde. (e.g., commercial paraformaldehyde contains 0–5% water, typically 1–3%). If a reaction medium is used, it is a melt of the methylolated hydantoin product at reaction temperature. Thus, no separation step, e.g., filtration, drying, etc., is needed after reaction in order to obtain a useful product. Because the product is a pure, dry solid, it can be transported more economically than the aqueous solutions previously known in the art. The product can be dissolved easily into a solution at ambient temperature, if desired. Because the product contains essentially no water, it may be incorporated into non-aqueous systems, an obstacle not easily overcome with products made in the conventional water-based processes.

A preferred hydantoin reactant for this method is 5,5-dimethylhydantoin, which produces 1,3-dimethylol-5,5-dimethylhydantoin, (DMDMH). This product can be used as a cosmetic preservative, functioning as a formaldehyde-donating antimicrobial agent, as well as for a variety of other purposes.

Other objects, features, and characteristics of the invention will become apparent upon consideration of the following description and claims.

DETAILED DESCRIPTION OF THE INVENTION

The process of our invention comprises reacting a hydantoin and a source of formaldehyde, preferably paraformaldehyde, in the presence of an alkaline catalyst and in the effective absence of water (the water content of the reactant mixture, including any water associated with the formaldehyde, typically is no more than about 1 weight percent), at conditions sufficient to induce reaction, resulting in the production of a methylolated hydantoin. The methylolated product, either added or formed by initial reaction and which is a melt at reaction temperature, becomes the medium in which total reaction readily takes place.

Paraformaldehyde, a non-aqueous formaldehyde polymer with the chemical formula $HO-(CH_2O)_n-H$ (n is about 8–100), is well known in the art.

Typical alkaline catalysts are alkali metal and alkaline earth metal salts such as sodium carbonate, sodium bicarbonate, calcium bicarbonate and sodium hydroxide, which are known and readily available. Other suitable alkaline catalysts are also within the scope of the invention.

The hydantoin reactants, many of which are well known in the art, typically include 5,5-dimethylhydantoin, 1-monomethylol-5,5-dimethylhydantoin, and 5-ethyl-5-methylhydantoin, which can be reacted separately or in combination. Corresponding products include 1,3-dimethylol-5,5-dimethylhydantoin, 1- or 3-methylol-5,5-dimethylhydantoin, 1,3-dimethylol-5-ethyl-5-methylhydantoin and 1- or 3-methylol-5-ethyl-5-methylhydantoin.

Additional hydantoin reactants that may be used include hydantoins which will react with non-aqueous formaldehyde in the presence of an alkaline catalyst and in the effective absence of water or any other reaction medium except for the product. Preferred hydantoins are those that will react with paraformaldehyde at temperatures between about 80° and 120° C. at atmospheric pressure. The reaction is slower at temperatures below about 80° C. at atmospheric pressure. In a reaction at atmospheric pressure and a temperature greater than about 120° C., the increased rate of thermal decomposition of formaldehyde may result in vaporization of some of the formaldehyde before it reacts with hydantoin, thereby decreasing the efficiency of the process. If the reaction is conducted at a pressure other than atmospheric pressure, suitable and preferable temperature ranges will depend upon the rates of the decomposition of paraformaldehyde, the reaction of paraformaldehyde with a hydantoin, and the vaporization of paraformaldehyde at that pressure.

Other, preferred candidates for reaction by this process at atmospheric pressure would also include those hydantoins per se with melting points in the temperature range of about 80°–120° C. The medium in these cases would be the melt form of the reactant. The spirit of the invention is the same, i.e., a product in essentially 100% active form is obtained on combination of nothing more than the reactants and catalyst. The resulting methylolated hydantion product contains less than 0.1 weight percent free formaldehyde. Thus, hydantoins with melting points to about 120° C. or the methylolated products of which melt to about 120° C. may be reacted in this process. For example, 5-methyl-5-hexylhydantoin, M.P. 108° C., may be reacted with paraformaldehyde by this process. Also, 5,5-diethylhydantoin (M.P. 167° C.) may be reacted since the methylolated product melts <100° C. Other hydantoins, such as 5,5-pentamethylene hydantoin (I), alkoxyalkyl derivative (II), or 5-alkyl derivatives (III),

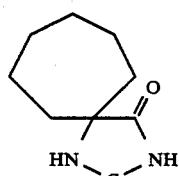

I

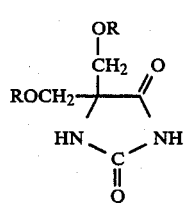

II

-continued

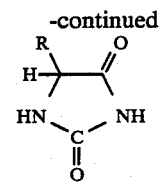

III all represent potential candidates for processing by this invention. Other N-substituted hydantoins, e.g., a 1- or 3- N-alkylated/arylated hydantoins, or further substituted 5-alkyl hydantoins, which meet the melt criteria, are candidates for this process. All of the above compounds, as well as others not specifically disclosed, are within the spirit of the invention.

Accordingly, products which are formed using these various reactants are within the scope of this invention. Condensation products of hydantoin and paraformaldehyde in the present invention generally are methylolated hydantoins which contain 1, or, more likely, 2 moles of formaldehyde. The products of this invention may also include methylolated hydantoins formed by the addition of more than 2 moles of formaldehyde per mole of hydantoin, such as 1-methylol-3-methyloloxymethylene-5,5-dimethylhydantoin, and 1,3-dimethyloloxymethylene-5,5-dimethylhydantoin.

In a typical process of this invention, hydantoin and commercially available paraformaldehyde are combined with a small amount of catalyst and the mixture is melted. If a methylolated hydantoin is used as a reaction diluent, it is melted, preferably at about 100° C., and is then mixed with the reactants and the catalyst. Alternatively, it is premixed as a solid with the reactants before heating. The mixture is allowed to react completely and is then cooled to room temperature, causing crystallization of the hydantoin-formaldehyde adduct.

We have found that the reactant ratio of 2 moles of formaldehyde per mole of dimethylhydantoin results in almost complete combining of the paraformaldehyde.

The quantity of catalyst needed for this reaction is small, and need comprise only about 0.1 weight percent of the reactant mixture. If any water is present in the catalyst or other ingredients, it is preferably an insignificant amount such as less than about 1% by weight of the total mixture.

The reaction is efficiently conducted at atmospheric pressure and at about 80°–120° C., or more preferably at about 80°–100° C. However, the process is not limited to these conditions, as explained above.

The reactants can be heated in any suitable manner, for example, in an oil bath. The reactants may be mixed before heating, such as on a ball mill.

At the conclusion of the reaction, purifying means, such as a vacuum, may be applied to the reaction mixture, preferably at reaction temperature, to essentially eliminate any moisture or residual formaldehyde odor that might exist prior to application of the purifying means. It is noted that this step is not essential to the production of commercially useful methylolated hydantoins using the method of this invention.

The following examples are offered in order to more fully illustrate the invention, but are not to be construed as limiting the scope thereof.

EXAMPLE 1

64.1 g (0.5 moles) of dimethylhydantoin (DMH) (Dantoin DMH, 40-683), 30.8 g of paraformaldehyde having a formaldehyde content of 97 wt % (1.0 moles formaldehyde) (Celanese Paraformaldehyde, High Assay, Prill/Powder), and 0.1 g anhydrous sodium carbonate (e.g., Baker reagent) were combined in a 250 ml round bottom flask. The flask was rotated while the dry mixture was heated in an oil bath at 100° C. After about 15 minutes the mixture was a melt, and after a total of 45 minutes the reaction was complete. The molten product was discharged to trays for 3–4 hours for crystallization at room temperature, and was then analyzed using conventional techniques. The resulting product was found to contain $\geq 31.3\%$ combined formaldehyde ($\geq 98\%$ of the theoretical combined formaldehyde) and $\geq 97\%$ DMDMH, with a melting range of 95°–100° C.

EXAMPLE 2

222.2 g of solid DMDMH (e.g., that obtained in example 1) was placed in a 1200 ml SS beaker. The beaker was immersed in an oil bath at 100° C. and the DMDMH was mechanically stirred as it melted, which required about 15 minutes. At this point, 2.7 g of a 4% sodium hydroxide solution was added, followed by the gradual addition over a 20 minute period of a preblended mixture of 446.4 g of DMH and 231.3 g of paraformaldehyde (97 wt % formaldehyde). During the addition the temperature of the mixture dropped to as low as 85° C. The mixture was stirred for an additional 45 minutes, and then was discharged into a foil-lined glass tray for solidification. The product was analyzed and was found to contain 31.4% combined formaldehyde and 96% DMDMH.

EXAMPLE 3

64.1 g (0.5 moles) of DMH, 30.8 g of paraformaldehyde (97 wt % formaldehyde (1.0 moles)) and 0.1 g anhydrous sodium bicarbonate (e.g., Baker reagent) were placed in a 16 oz. jar, which was then turned on a ball mill for about 45 minutes. The mixture was transferred to a 250 ml round-bottom flask, which was rotated while being heated in an oil bath at 80° C. The mixture changed from a free-flowing solid blend to a flowable slurry and finally to a liquid in about 45 minutes. At this point a sample of the product was analyzed and found to contain 95% DMDMH. The reaction was allowed to continue for another 30 minutes, at which time the product began to solidify. Analysis showed 31.0% combined formaldehyde and 97% DMDMH.

EXAMPLE 4

79.1 g (0.5 moles) of monomethyloldimethylhydantoin (Dantoin MDMH, 40-685), 15.1 g of paraformaldehyde (97 wt % formaldehyde (0.5 moles)) and 0.1 g of anhydrous sodium bicarbonate were combined in a 250 ml round-bottom flask. The flask was rotated while the mixture was heated in an oil bath at 100° C. The dry mixture slowly changed from a solid to a liquid in about 20 minutes, and the reaction was complete after about 35 minutes. The molten product was discharged into a tray and allowed to crystallize over a 4-hour period while cooling to room temperature. Analysis of the product showed 30.5% combined formaldehyde and 86% DMDMH.

EXAMPLE 5

71.7 g (0.5 moles) of 5-ethyl-5-methylhydantoin (EMH) (Dantoin EMH, 40-747), 30.8 g of paraformaldehyde (97 wt % formaldehyde (1.0 moles)) and 0.1 g anhydrous sodium bicarbonate were placed in a 250 ml round-bottom flask, which was rotated while being heated in an oil bath at 100° C. The mixture was completely melted in about 30 minutes. After another 15 minutes at reaction temperature, the product was discharged into a container for storage. Crystallization was slow. After 2 months some liquid still remained. Analysis showed >28% combined formaldehyde (>95% of the theoretical combined formaldehyde).

EXAMPLE 6

32.0 g (0.25 moles) DMH, 35.6 g (0.25 moles) of EMH, 30.8 g of paraformaldehyde (97 wt % formaldehyde (1.0 moles)) and 0.1 g anhydrous sodium bicarbonate were placed in a 250 ml round-bottom flask. The flask was rotated while being heated to 100° C. The mixture was completely melted in about 20 minutes. After 45 minutes, the mixture was discharged into a container for storage. Crystallization was slow. The first crystals did not appear for several days. Analysis showed >29% combined formaldehyde (>95% of the theoretical combined formaldehyde).

While the invention has been described in relation to certain illustrative embodiments, it is to be understood that the invention is not limited to the disclosed embodiments. On the contrary, many modifications and substitutions may be made within the spirit and scope of the appended claims. For example, the reactions and the reactant ratios may be varied to produce products other than those disclosed in the examples, such as methylolated hydantoins carrying less than two or more than two formaldehyde molecules. Furthermore, the invention may comprise, consist or consist essentially of the steps and materials recited herein.

We claim:

1. A method for the production of a methylolated hydantoin which comprises reacting a hydantoin, a source of formaldehyde, and an alkaline catalyst in the effective absence of water at conditions of temperature and pressure sufficient to produce said methylolated hydantoin.

2. A method according to claim 1 wherein the source of formaldehyde is paraformaldehyde.

3. A method according to claim 2 wherein said hydantoin and paraformaldehyde reactants are mixed in a mole ratio of about 1 mole of hydantoin per 1 or 2 moles of formaldehyde.

4. A method according to claim 3 wherein the amount of water in the reactant mixture is no more than about 1 weight percent.

5. A method according to claim 4 wherein said alkaline catalyst is selected from the group consisting of sodium carbonate, sodium bicarbonate, and sodium hydroxide.

6. A method according to claim 5 wherein said alkaline catalyst comprises approximately 0.1 weight percent of the total amount of reactants.

7. A method according to claim 1 wherein said hydantoin reactant is selected from the group consisting of 5,5-dimethylhydantoin, 1-methylol-5,5-dimethylhydantoin, 3-methylol-5,5-dimethylhydantoin, and 5-ethyl-5-methylhydantoin.

8. A method according to claim 1 wherein said methylolated hydantoin is in essentially 100% active form.

9. A method according to claim 8 wherein said methylolated hydantoin product contains less than 0.1 weight percent free formaldehyde.

10. A method according to claim 9 wherein no separation step is required.

11. A method according to claim 1 wherein said methylolated hydantoin product is selected from the group consisting of 1,3-dimethylol-5,5-dimethylhydantoin and 1,3-dimethylol-5-ethyl-5-methylhydantoin.

12. A method according to claim 1 wherein molten 1,3-dimethylol-5,5-dimethylhydantoin is used as a reaction medium.

13. A method according to claim 12 wherein the mole ratio of said reaction medium to hydantoin reactant is about 1:1 or less when the reaction begins.

14. A method according to claim 13 wherein the reaction is conducted at atmospheric pressure and the starting reaction temperature is at least 80° C.

15. A method according to claim 1 wherein the reaction is initiated in the absence of a reaction medium.

16. A method according to claim 15 wherein the reaction is conducted at atmospheric pressure and the starting reaction temperature is at least 80° C.

17. A method according to claim 15 wherein the reactants are stirred for about 45 minutes and then heated to at least 80° C. at atmospheric pressure.

18. A method according to claim 1 further comprising the step of removing residual moisture or odor from said methylolated hydantoin.

19. A method according to claim 18 wherein said residual moisture or odor is removed using a vacuum.

20. A method for the production of a crystallized methylolated hydantoin which comprises mixing a hydantoin, a source of formaldehyde and an alkaline catalyst in the effective absence of water, heating said mixture until reaction is complete and cooling said mixture until crystallization of methylolated hydantoin occurs.

* * * * *

UNITED STATES PATENT AND TRADEMARK OFFICE
CERTIFICATE OF CORRECTION

PATENT NO. : 4,908,456

DATED : March 13, 1990

INVENTOR(S) : FARINA, et al.

It is certified that error appears in the above-identified patent and that said Letters Patent is hereby corrected as shown below:

Title Page:

[73] Assignee: LONZA, INC., Fairlawn, New Jersey

Signed and Sealed this

Second Day of July, 1991

Attest:

HARRY F. MANBECK, JR.

Attesting Officer

Commissioner of Patents and Trademarks